US012668588B2

(12) United States Patent
Wu et al.

(10) Patent No.: US 12,668,588 B2
(45) Date of Patent: Jun. 30, 2026

(54) METHOD FOR PREPARING INTERMEDIATE OF URACIL COMPOUND CONTAINING ISOXAZOLINE

(71) Applicants: SHENYANG SINOCHEM AGROCHEMICALS R&D CO., LTD., Shenyang (CN); JIANGSU YANGNONG CHEMICAL CO., LTD., Yangzhou (CN)

(72) Inventors: Enming Wu, Shenyang (CN); Gongxin Wu, Shenyang (CN); Chunrui Yu, Shenyang (CN); Qiao Wu, Shenyang (CN); Jichun Yang, Shenyang (CN); Yanming Ye, Shenyang (CN); Fuqiang Yu, Shenyang (CN); Youren Xue, Shenyang (CN); Aiying Guan, Shenyang (CN)

(73) Assignees: SHENYANG SINOCHEM AGROCHEMICALS R&D CO., LTD., Shenyang (CN); JIANGSU YANGNONG CHEMICAL CO., LTD., Yangzhou (CN)

( * ) Notice: Subject to any disclaimer, the term of this patent is extended or adjusted under 35 U.S.C. 154(b) by 705 days.

(21) Appl. No.: 18/004,147

(22) PCT Filed: Jun. 30, 2021

(86) PCT No.: PCT/CN2021/103484

§ 371 (c)(1),
(2) Date: Jan. 3, 2023

(87) PCT Pub. No.: WO2022/002117

PCT Pub. Date: Jan. 6, 2022

(65) Prior Publication Data

US 2023/0265084 A1 Aug. 24, 2023

(30) Foreign Application Priority Data

Jul. 2, 2020 (CN) ........................ 202010633453.3

(51) Int. Cl.
*C07D 413/10* (2006.01)
*B01J 31/02* (2006.01)

(52) U.S. Cl.
CPC ........ *C07D 413/10* (2013.01); *B01J 31/0244* (2013.01)

(58) Field of Classification Search
CPC .................................................... C07D 413/10
See application file for complete search history.

(56) References Cited

U.S. PATENT DOCUMENTS

| | | | | |
|---|---|---|---|---|
| 6,992,044 B1 * | 1/2006 | Andree | C07D 413/10 544/55 |
| 2018/0230139 A1 * | 8/2018 | Liu | C07D 413/10 |
| 2023/0053699 A1 * | 2/2023 | Lian | A01N 43/80 |

FOREIGN PATENT DOCUMENTS

| | | | | | |
|---|---|---|---|---|---|
| CN | 1283190 | A | | 2/2001 | |
| CN | 105753853 | A | | 7/2016 | |
| CN | 110818644 | A | | 2/2020 | |
| DE | 19543676 | A1 | | 11/1996 | |
| JP | 10218862 | A | * | 8/1998 | |
| JP | 2002193914 | A | | 7/2002 | |
| WO | 0190058 | A1 | | 11/2001 | |
| WO | 2016095768 | A1 | | 6/2016 | |
| WO | WO-2021088856 | A1 | * | 5/2021 | C07D 413/14 |

OTHER PUBLICATIONS

Albert W. Lutz et al., Novel 6-(trifluoromethyl)cytosines and 6-(trifluoromethyl)uracils, Journal of Heterocyclic Chemistry, Jun. 1972, vol. 9, Issue 3, pp. 513-522.

* cited by examiner

*Primary Examiner* — Matthew P Coughlin
(74) *Attorney, Agent, or Firm* — NKL Law; Allen Xue

(57) ABSTRACT

A method for preparing an intermediate of a uracil compound containing isooxazoline includes the steps of: making 3-amino-4,4,4-trifluorocrotonic acid methyl ester react with substituted aryl carbamate; in a reaction process, continuously evaporating water and byproduct alcohol in the system; and conducting processing to obtain the intermediate of the uracil compound containing isooxazoline. Using this method the selectivity of the reaction and the utilization rate of raw materials are improved; the hydrolysis products, impurities and tar are reduced; the reaction time is greatly shortened; and the productivity is improved. After one recrystallization of crude products, an intermediate product with purity of more than 97% can be obtained, and quantitative yield can be more than 85%.

11 Claims, No Drawings

METHOD FOR PREPARING INTERMEDIATE OF URACIL COMPOUND CONTAINING ISOXAZOLINE

TECHNICAL FIELD

The present invention relates to a preparation method of a class of herbicide intermediates, in particular to a method for preparing an intermediate of a uracil compound containing isoxazoline.

BACKGROUND

Patent WO2016095768 has reported that the compound of general formula I can effectively control the barnyard grass, green bristlegrass, sedges, water sedge, *Digitaria sanguinalis* (L.) Scop., hispid arthraxon, piemarker, *zinnia, Amaranthus retroflexus*, purslane, *Xanthium strumarium, Solanum nigrum* L., *Cassia tora* Linn., *Hibiscus trionum* L., *Glycine soja* and other weeds, can obtain good weeding effect in low doses, and can be used as a herbicide in agriculture.

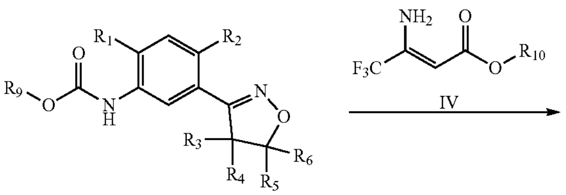

IV

III

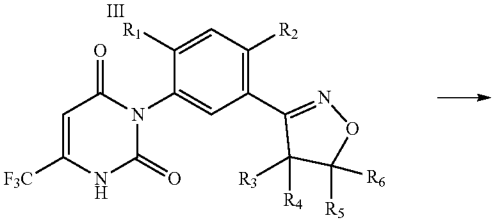

II

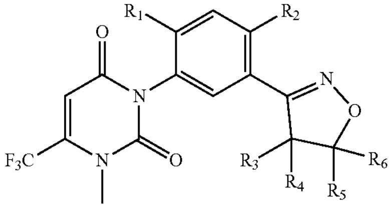

I

The compound of general formula II is an intermediate of the compound of general formula I.

Although the compound of general formula I has excellent herbicidal activity, part of the compound of general formula I is oily at room temperature, and is difficult to be purified by recrystallization, distillation and other industrial methods, resulting in more impurities, low content and poor appearance of the product and affecting the use of the product. Therefore, a method for preparing high-content compounds of general formula II is needed. The compound of general formula I is synthesized through the high-content compounds of general formula II, and the compound of general formula I can meet the requirements without further purification. Although the compound of general formula II can meet the content requirement through multiple recrystallization, it will undoubtedly greatly reduce the yield of the product and increase the cost and three wastes. Therefore, a method for preparing an intermediate of a uracil compound containing isoxazoline with general formula II at high yield and high content is needed.

Patent WO2016095768 discloses a synthesis method of the compound of general formula II, but the cycloidal reagents used, such as dichloromethane dimethyl ammonium chloride, are not commercially available and expensive, so industrial production cannot be realized.

Reference patent document DE19543676 discloses a preparation method of analogs of the compound of general formula II. The method uses high boiling point aprotic polar solvent N,N-dimethylformamide or N-methylpyrrolidone as a solvent and potassium carbonate as alkali to react and distill to remove the generated ethanol. After the reaction, the solvent is removed by decompression, and the mixture is acidized and recrystallized to obtain the target product. The first disadvantage of the method is that trace water in the reaction system cannot be effectively removed from the system, and trace water may cause serious hydrolysis of the raw material compound of general formula III, resulting in decrease of the utilization rate of the raw material and yield loss. The second disadvantage is that N,N-dimethylformamide or N-methylpyrrolidone as the solvent causes poor reaction selectivity and more impurities, and the product needs to recrystallize several times, resulting in the massive increase of three wastes.

Reference patent JP2002193914A improves the above method. The mixed solvent system of N, N-dimethylformamide and toluene with respective mass fraction of 50% is used for reflux and water removal, and potassium carbonate is used as alkali. After the reaction, the solvent is removed by decompression, and the mixture is acidified and washed to obtain the target product. Although the water in the system is removed by the disclosed method to a certain extent and the hydrolyzed products are inhibited, the whole reaction also took too long due to the addition of toluene, a non-polar water-carrying agent, resulting in the decomposition of the intermediate of the compound of general formula III to different degrees. Thus, the products have more impurities and tar content. Post-treatment requires multiple recrystallization to obtain the content above 95% and the production efficiency is also greatly reduced.

Therefore, in the field, it is hoped to obtain a method that can well inhibit substrate hydrolysis, speed up the reaction, reduce the production of impurities and tar, and facilitate the preparation of the intermediate of the uracil compound containing isoxazoline with high yield and high content.

SUMMARY

In order to overcome the defects of the prior art, the purpose of the present invention is to provide a method for preparing an intermediate of a uracil compound containing isoxazoline with high yield and high content.

To realize the above purpose, the technical solution of the present invention is as follows:

A method for preparing an intermediate of a uracil compound containing isoxazoline comprises: making 3-amino-4,4,4-trifluorocrotonic acid methyl ester react with substituted aryl carbamate; in a reaction process, continuously evaporating water and byproduct alcohol in the system; and conducting processing to obtain the intermediate of the uracil compound containing isooxazoline;

or, making 3-amino-4,4,4-trifluorocrotonic acid methyl ester react with substituted aryl carbamate in the presence of a catalyst; in a reaction process, continuously evaporating water and byproduct alcohol in the system; and conducting processing to obtain the intermediate of the uracil compound containing isooxazoline.

A reaction formula is:

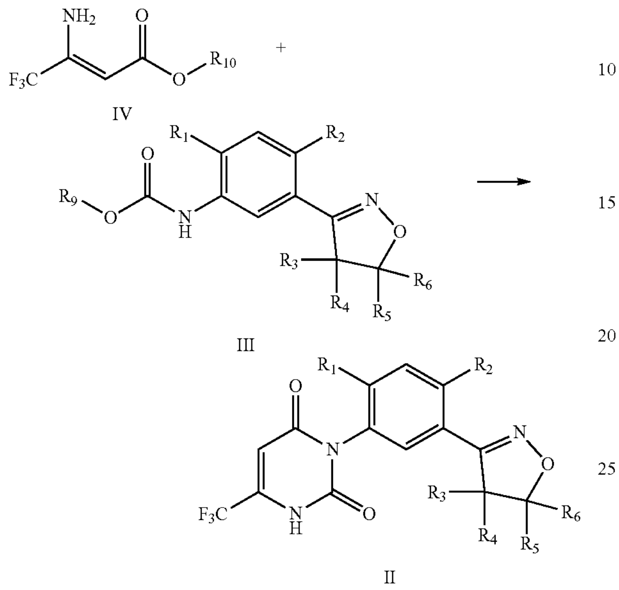

$R_1$ and $R_2$ can be the same or different, and are respectively selected from hydrogen, fluorine or chlorine;

$R_3$ is selected from hydrogen or $C_1$-$C_4$ alkyl;

$R_4$ is selected from hydrogen, $CO_2R_7$ or $CH_2OR_8$;

$R_5$ is selected from hydrogen, $CO_2R_7$ or $CH_2OR_8$;

$R_6$ is selected from hydrogen, $C_1$-$C_4$ alkyl or $C_1$-$C_4$ haloalkyl;

$R_7$ is selected from $C_1$-$C_4$ alkyl, $C_1$-$C_4$ haloalkyl, allyl or propargyl;

$R_8$ is selected from hydrogen, $C_1$-$C_4$ alkyl, $C_1$-$C_4$ haloalkyl or $C_1$-$C_4$ alkyl carbonyl;

$R_9$ is selected from $C_1$-$C_4$ alkyl;

$R_{10}$ is selected from $C_1$-$C_4$ alkyl.

Preferably, $R_1$ and $R_2$ can be the same or different, and are respectively selected from hydrogen, fluorine or chlorine;

$R_3$ is selected from hydrogen or $C_1$-$C_4$ alkyl;

$R_4$ is selected from hydrogen;

$R_5$ is selected from $CO_2R_7$;

$R_6$ is selected from hydrogen, $C_1$-$C_4$ alkyl or $C_1$-$C_4$ haloalkyl;

$R_7$ is selected from methyl, ethyl, n-propyl, n-butyl, isopropyl, isobutyl, tert-butyl, trifluoroethyl, allyl and propargyl;

$R_9$ is selected from methyl or ethyl;

$R_{10}$ is selected from methyl or ethyl.

The compound shown in formula III and the compound shown in formula IV react in the presence of a water carrying agent or a mixed solvent. In the reaction process, the water and byproduct alcohol in the system are continuously evaporated, and the intermediate of the uracil compound containing isooxazoline is obtained after treatment; or, the reaction process is carried out under the action of a catalyst.

Alkali is added in the reaction process, wherein the molar ratio of the alkali to the compound shown in formula III is 0.5:1-3:1.

The catalyst is 1,8-diazabicyclo[5.4.0]undec-7-ene, salt of 1,8-diazabicyclo[5.4.0]undec-7-ene or solution of 1,8-diazabicyclo[5.4.0]undec-7-ene, preferably 1,8-diazabicyclo[5.4.0]undec-7-ene, wherein the use amount of the catalyst is 0.001%-10% of the weight of the compound shown in formula III.

The use amount of the catalyst is 0.1%-5% of the weight of the compound shown in formula III.

The alkali is one or two of potassium carbonate, sodium carbonate, cesium carbonate, potassium bicarbonate, sodium bicarbonate or cesium bicarbonate.

The alkali is one or two of potassium carbonate, sodium carbonate, potassium bicarbonate and sodium bicarbonate, wherein the molar ratio of the alkali to the compound shown in formula III is 0.5:1-2:1.

The amount of the water carrying agent or mixed solvent is 2-20 times the weight of the compound shown in formula III;

The mixed solvent comprises the water carrying agent and a polar aprotic solvent, wherein the weight of the polar aprotic solvent in the mixed solvent is 20%-70%.

The water carrying agent is one of n-propyl acetate, isopropyl acetate, n-butyl acetate, methyl isopropyl ketone, methyl isobutyl ketone, ethylene glycol dimethyl ether, ethylene glycol diethyl ether, 2-methyl tetrahydrofuran and acetonitrile.

The water carrying agent in the mixed solvent is one of toluene, chlorobenzene, n-propyl acetate, isopropyl acetate, methyl isopropyl ketone, methyl isobutyl ketone, ethylene glycol dimethyl ether, ethylene glycol diethyl ether, 2-methyltetrahydrofuran and acetonitrile; and the polar aprotic solvent in the mixed solvent is N,N-dimethylformamide, dimethyl sulfoxide or N-methylpyrrolidone.

Preferably, the amount of the water carrying agent or mixed solvent is 3-8 times the weight of the compound shown in formula III;

The mixed solvent comprises the water carrying agent and the polar aprotic solvent, wherein the weight of the polar aprotic solvent in the mixed solvent is 30%-60%.

The water carrying agent or mixed solvent may be further preferably as follows: the water carrying agent is preferably one of isopropyl acetate, methyl isobutyl ketone and acetonitrile, and the mixed solvent is preferably a mixed solvent of one of water carrying agents of toluene, n-propyl acetate, isopropyl acetate, methyl isobutyl ketone, 2-methyltetrahydrofuran and acetonitrile and one of polar aprotic solvents of N,N-dimethylformamide, dimethyl sulfoxide or N-methylpyrrolidone.

The initiator of general formula IV is known or can be prepared by known methods (see J. Hetercycl. Chem. 9 (1972), 513-522).

The compound of general formula III can be prepared according to the method in patent DE19543676.

In the compounds of general formulas (I, II, III, IV) given above, the terms used are generally defined as follows: alkyl refers to the straight chain or branched chain form, such as methyl, ethyl, n-propyl, isopropyl, n-butyl, isobutyl and other groups. Haloalkyl: straight or branched alkyls on which hydrogen atoms may be partially or wholly replaced by halogens, such as chloromethyl, dichloromethyl, trichloromethyl, fluoromethyl, difluoromethyl and trifluoromethyl. Alkyl carbonyl: Alkyls are connected to structures by carbonyls, such as $CH_3CO$— or $CH_3CH_2CO$—.

The present invention has the advantages:

In the present invention, by selecting the water carrying agent or the mixed solvent, the water and the alcohol in the system can be continuously removed, the hydrolysis of raw materials and products is reduced, and the selectivity of the reaction is improved. More importantly, the addition of the catalyst greatly reduces the reaction time. Under the combined action of the two, the selectivity of the reaction and the utilization rate of raw materials are improved; the hydrolysis products, impurities and tar are reduced; the reaction time is greatly shortened; and the productivity is greatly improved. Moreover, after one recrystallization of crude products, an intermediate product with purity of more than 97% can be obtained, and quantitative yield can be more than 85%, which meets the requirements of synthetic products and is convenient for industrial production.

DETAILED DESCRIPTION

The preparation method of the compound shown in formula II is further detailed below by enumerating embodiments, but the present invention is not limited to these embodiments. Various changes and variations may be made to the present invention for those skilled in the art. Any modification, equivalent substitution, improvement, etc. made within the spirit and principles of the present invention shall be included within the protection scope of the present invention.

In the method of the present invention, the selectivity of the reaction and the utilization rate of raw materials are improved; the hydrolysis products, impurities and tar are reduced; the reaction time is greatly shortened; and the productivity is improved. Moreover, after one recrystallization of crude products, an intermediate product with purity of more than 97% can be obtained, and quantitative yield can be more than 85%, which is suitable for industrial production.

Embodiment 1 Synthesis of Compound II-1

39.3 g (100 mmol) of 3-(2-chloro-5-((ethoxycarbonyl) amino)-4-fluorophenyl)-5-methyl-4,5-dihydroisoxazole-5-carboxylate ethyl, 19.2 g (103 mmol) of 3-amino-4,4,4-trifluorocrotonate, 10.4 g (75 mmol) of potassium carbonate, 80 g of isopropyl acetate, 80 g of N,N-dimethylformamide and 1.0 g of 1,8-diazabicyclo[5.4.0]undec-7-ene were added to a reaction flask with a rectification device, stirred, heated and subjected to reflux reaction for 5 hours; in this period, a small amount of low-boiling-point substances below 78° C. were separated from the top of the tower; HPLC was used for tracking until the reaction was ended; most solvents were evaporated under reduced pressure; residues were acidified with hydrochloric acid; pH was adjusted to 2-4; isopropyl acetate was added for extraction; after stirring for 20 minutes, the lower water layer was removed; the organic layer was washed with water once; after the water layer was removed, isopropyl acetate was evaporated under reduced pressure; residues were normalized by HPLC and the content was 96.1%; the mixture was recrystallized with ethanol water, and filtered at 0-5° C.; a filter cake was drip-washed with cold ethanol water and dried to obtain 41.3 g; HPLC quantitative content was 98.3%; and quantitative yield was 87.5%.

Embodiment 2 Synthesis of Compound II-1

39.3 g (100 mmol) of 3-(2-chloro-5-((ethoxycarbonyl) amino)-4-fluorophenyl)-5-methyl-4,5-dihydroisoxazole-5-carboxylate ethyl, 19.2 g (103 mmol) of 3-amino-4,4,4-trifluorocrotonate, 10.4 g (75 mmol) of potassium carbonate, 120 g of methyl isobutyl ketone and 1.0 g of 1,8-diazabicyclo[5.4.0]undec-7-ene were added to a reaction flask with a rectification device, stirred, heated and subjected to reflux reaction for 10 hours; in this period, a small amount of low-boiling-point substances below 78° C. were separated from the top of the tower; HPLC was used for tracking until the reaction was ended; most solvents were evaporated under reduced pressure; residues were acidified with hydrochloric acid; pH was adjusted to 2-4; methyl isobutyl ketone was added for extraction; after stirring for 20 minutes, the lower water layer was removed; the organic layer was washed with water once; after the water layer was removed, methyl isobutyl ketone was evaporated under reduced pressure; residues were normalized by HPLC and the content was 95.0%; the mixture was recrystallized with ethanol water, and filtered at 0-5° C.; a filter cake was drip-washed with cold ethanol water and dried to obtain 41.7 g; HPLC quantitative content was 96.0%; and quantitative yield was 86.3%.

Embodiment 3 Synthesis of Compound II-2

39.3 g (100 mmol) of (3-(2-chloro-4-fluoro-5-((methoxycarbony)amino)phenyl)-5-methyl-4,5-dihydroisoxazole-5-yl) methylacetate, 19.2 g (103 mmol) of 3-amino-4,4,4-trifluorocrotonate, 9.1 g (65 mmol) of potassium carbonate, 80 g of isopropyl acetate, 80 g of N-methylpyrrolidone and 1.0 g of 1,8-diazabicyclo[5.4.0]undec-7-ene were added to a reaction flask with a rectification device, stirred, heated and subjected to reflux reaction for 5 hours; in this period, a small amount of low-boiling-point substances below 78° C. were separated from the top of the tower; HPLC was used for tracking until the reaction was ended; most solvents were evaporated under reduced pressure; residues were acidified with hydrochloric acid; pH was adjusted to 2-4; isopropyl acetate was added for extraction; after stirring for 20 minutes, the lower water layer was removed; the organic layer was washed with water once; after the water layer was removed, isopropyl acetate was evaporated under reduced pressure; residues were normalized by HPLC and the content was 95.1%; the mixture was recrystallized with ethanol water, and filtered at 0-5° C.; a filter cake was drip-washed with cold ethanol water and dried to obtain 42.0 g; HPLC quantitative content was 97.1%; and quantitative yield was 87.9%.

Embodiment 4 Synthesis of Compound II-2

39.0 g (100 mmol) of (3-(2-chloro-5-((methoxycarbony) amino)-4-fluorophenyl)-5-methyl-4,5-dihydroisoxazole-5-yl) methylacetate, 19.2 g (103 mmol) of 3-amino-4,4,4-trifluorocrotonate, 3.0 g of tetrabutylammonium bromide, 9.1 g (65 mmol) of potassium carbonate, 80 g of toluene and 80 g of N,N-dimethylformamide were added to a reaction flask with a rectification device, stirred, heated and subjected to reflux reaction for 25 hours; in this period, a small amount of low-boiling-point substances below 80° C. were separated from the top of the tower; HPLC was used for tracking until the reaction was ended; most solvents were evaporated under reduced pressure; residues were acidified with hydrochloric acid; pH was adjusted to 2-4; toluene was added for extraction; after stirring for 20 minutes, the lower water layer was removed; the organic layer was washed with water once; after the water layer was removed, toluene was evaporated under reduced pressure; residues were normalized by HPLC and the content was 86%; the mixture was recrystallized with ethanol water for three times, and filtered at 0-5° C.; a filter cake was drip-washed with cold ethanol water and dried to obtain 24.2 g; HPLC quantitative content was 96.1%; and quantitative yield was 50.1%.

Embodiment 5 Synthesis of Compound II-2

3.1 Kg (8 mol) of (3-(2-chloro-4-fluoro-5-((methoxycarbony)amino)phenyl)-5-methyl-4,5-dihydroisoxazole-5-yl) methylacetate, 1.5 Kg (8.1 mol) of 3-amino-4,4,4-trifluorocrotonate, 0.75 Kg (5.5 mol) of potassium carbonate, 70 Kg of isopropyl acetate, 60 Kg of N,N-dimethylformamide and 0.06 Kg of 1,8-diazabicyclo[5.4.0]undec-7-ene were added to a reaction flask with a rectification device, stirred, heated and subjected to reflux reaction for 5 hours; in this period, a small amount of low-boiling-point substances below 78° C. were separated from the top of the tower; HPLC was used for tracking until the reaction was ended; most solvents were evaporated under reduced pressure; residues were acidified with hydrochloric acid; pH was adjusted to 2-4; isopropyl acetate was added for extraction; after stirring for 20 minutes, the lower water layer was removed; the organic layer was washed with water once; after the water layer was removed, isopropyl acetate was evaporated under reduced pressure; residues were normalized by HPLC and the content was 94.5%; the mixture was recrystallized with ethanol water, and filtered at 0-5° C.; a filter cake was drip-washed with cold ethanol water and dried to obtain 3.3 Kg; HPLC quantitative content was 97.0%; and quantitative yield was 86.3%.

Embodiment 6 Synthesis of Compound I-3

33.4 g (0.07 mol, quantitative content of 97.2%) of above compound II-2 (3-(2-chloro-5-(2,6-dioxy-4-trifluoromethyl-3,6-dihydropyrimidine-1(2H)-yl)-4-fluorophenyl)-5-methyl-4,5-dihydroisoxazole-5-yl) methylacetate, 7.10 g (0.084 mol) of sodium bicarbonate, 150 g of dichloromethane and 3.0 g of 1, 4-diazadicyclic [2.2.2] octane were added to an autoclave; 5.0 g of methyl chloride was measured and introduced; the mixture was stirred and heated to 70-80° C.; a pressure gauge showed 0.4 Mpa; and the reaction lasted for 11 hours. The temperature was lowered to 20° C., the pressure in the autoclave was discharged, and the excess methyl chloride was recovered. 50 g of water was added to the autoclave and stirred for 10 minutes; after that, the mixture was layered and the water layer was removed; the organic layer was washed with 50 g of water once; the organic layer was filtered to remove a small amount of undissolved substances; the desolvent was decompressed to obtain 33.9 g of oil, with quantitative content of 93.5% and yield of 94.5%.

The specific structures of the compounds obtained in embodiments 1, 2, 3 and 4:

| No. | Structure | Nuclear magnetic data ($^1$HNMR, 300 MHz, internal standard TMS, solvent $CDCl_3$) |
|---|---|---|
| II-1 | 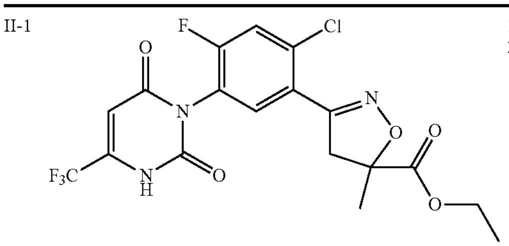 | 1.33(t, 3H), 1.71(s, 3H), 3.34(d, 1H), 3.60(d, 1H), 4.27(m, 2H), 6.21(s, 1H), 7.36(d, 1H), 7.71(d, 1H), 10.13(s, 1H). |
| II-2 | 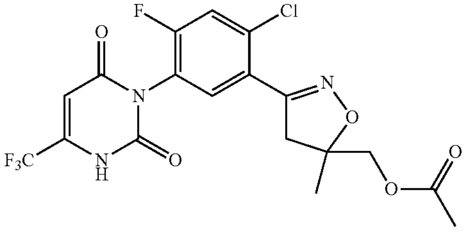 [SMILES: CC(=O)OCC1(C)CC(c2cc(-n3c(=O)cc(C(F)(F)F)[nH]c3=O)c(F)cc2Cl)=NO1] | 1.40(s, 3H), 2.02(s, 3H), 3.24(d, 1H), 3.49(d, 1H), 3.86(m, 2H), 6.21(s, 1H), 7.50(d, 1H), 7.69(d, 1H), 10.01(s, 1H). |
| I-3 | 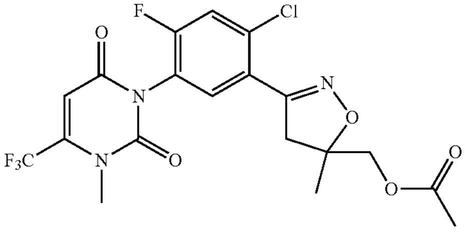 [SMILES: CC(=O)OCC1(C)CC(c2cc(-n3c(=O)cc(C(F)(F)F)n(C)c3=O)c(F)cc2Cl)=NO1] | 1.41(s, 3H), 2.03(s, 3H), 3.25(d, 1H), 3.50(d, 1H), 3.62(s, 3H), 3.88(m, 2H), 6.22(s, 1H), 7.51(d, 1H), 7.69(d, 1H). |

Reference Embodiment 1 Synthesis of Compound II-2

39.0 g (100 mmol) of (3-(2-chloro-5-(methoxycarbonyl) amino)-4-fluorophenyl)-5-methyl-4,5-dihydroisoxazole-5-yl) methylacetate, 19.2 g (103 mmol) of 3-amino-4,4,4-trifluorocrotonate, 9.1 g (65 mmol) of potassium carbonate and 100 g of N,N-dimethylformamide were added to a reaction flask with a rectification device, stirred, heated and subjected to reaction for 4 hours at 130° C.; HPLC was used for tracking until the reaction was ended; most solvents were evaporated under reduced pressure; residues were acidified with hydrochloric acid; pH was adjusted to 2-4; methyl isobutyl ketone was used for extraction; after stirring for 20 minutes, the lower water layer was removed; the organic layer was washed with water once; after the water layer was removed, methyl isobutyl ketone was evaporated under reduced pressure; residues were normalized by HPLC and the content was 42.2%;

Reference Embodiment 2 Synthesis of Compound II-2

39.0 g (100 mmol) of (3-(2-chloro-5-(methoxycarbonyl) amino)-4-fluorophenyl)-5-methyl-4,5-dihydroisoxazole-5-yl) methylacetate, 19.2 g (103 mmol) of 3-amino-4,4,4-trifluorocrotonate, 9.1 g (65 mmol) of potassium carbonate and 100 g of N,N-dimethylformamide were added to a reaction flask with a rectification device, stirred and heated; micro negative pressure was applied to the reaction system through the top of the tower; water and byproduct ethanol were removed from the reaction system, and the reaction was carried out at 105° C. for 18 hours; most solvents were evaporated under reduced pressure; residues were acidified with hydrochloric acid; pH was adjusted to 2-4; methyl isobutyl ketone was used for extraction; after stirring for 20 minutes, the lower water layer was removed; the organic layer was washed with water once; after the water layer was removed, methyl isobutyl ketone was evaporated under reduced pressure; residues were normalized by HPLC and the content was 64.3%;

It can be seen from the above embodiments and reference embodiments that the method for preparing the intermediate of the uracil compound containing isooxazoline is available in raw materials and mild in conditions; through the water carrying agent or the mixed solvent, the water and the alcohol in the system can be continuously removed, the hydrolysis of raw materials and products is reduced, and the selectivity of the reaction is improved. The addition of the catalyst greatly reduces the reaction time. Under the combined action of the two, the utilization rate of raw materials is improved; the hydrolysis products, impurities and tar are reduced; the reaction time is greatly shortened; and the productivity is greatly improved, which is convenient for industrial production.

The invention claimed is:

1. A method for preparing an intermediate of a uracil compound containing isooxazoline, comprising:

reacting a compound of formula III with a compound of formula IV in the presence of a catalyst; and continuously removing water and alcohol generated in the reaction by evaporation to obtain the intermediate of the uracil compound containing isooxazoline of formula II:

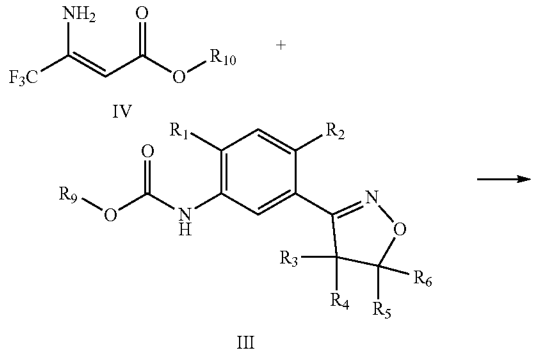

IV

III

-continued

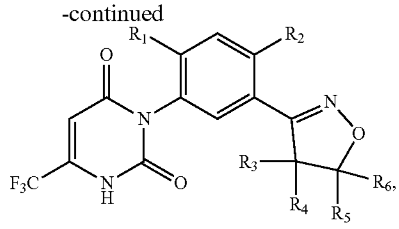

II wherein:

$R_1$ and $R_2$ are the same or different, and are independently selected from hydrogen, fluorine, and chlorine;

$R_3$ is hydrogen or $C_1$-$C_4$ alkyl;

$R_4$ is hydrogen, $CO_2R_7$, or $CH_2OR_8$;

$R_5$ is hydrogen, $CO_2R_7$, or $CH_2OR_8$;

$R_6$ is hydrogen, $C_1$-$C_4$ alkyl, or $C_1$-$C_4$ haloalkyl;

$R_7$ is $C_1$-$C_4$ alkyl, $C_1$-$C_4$ haloalkyl, allyl, or propargyl;

$R_8$ is hydrogen, $C_1$-$C_4$ alkyl, $C_1$-$C_4$ haloalkyl, or $C_1$-$C_4$ alkyl carbonyl;

$R_9$ is $C_1$-$C_4$ alkyl;

$R_{10}$ is $C_1$-$C_4$ alkyl, and the catalyst is 1,8-diazabicyclo[5.4.0]undec-7-ene or a salt thereof.

2. The method for preparing the intermediate of the uracil compound containing isooxazoline according to claim 1, wherein:

$R_1$ and $R_2$ are the same or different, and are independently selected from hydrogen, fluorine, and chlorine;

$R_3$ is hydrogen or $C_1$-$C_4$ alkyl;

$R_4$ is hydrogen;

$R_5$ is $CO_2R_7$;

$R_6$ is $C_1$-$C_4$ haloalkyl;

$R_7$ is selected from methyl, ethyl, n-propyl, n-butyl, isopropyl, isobutyl, tert-butyl, trifluoroethyl, allyl, and propargyl;

$R_9$ is methyl or ethyl; and $R_{10}$ is methyl or ethyl.

3. The method for preparing the intermediate of the uracil compound containing isooxazoline according to claim 1, wherein the reaction is carried out in the presence of an alkali, and a molar ratio of the alkali to the compound of formula III is 0.5:1-3:1.

4. The method for preparing the intermediate of the uracil compound containing isooxazoline according to claim 1, wherein an amount of the catalyst is 0.001%-10% of a weight of the compound of formula III.

5. The method for preparing the intermediate of the uracil compound containing isooxazoline according to claim 4, wherein the amount of the catalyst is 0.1%- 5% of the weight of the compound of formula III.

6. The method for preparing the intermediate of the uracil compound containing isooxazoline according to claim 3, wherein the alkali is one or two selected from the group consisting of potassium carbonate, sodium carbonate, cesium carbonate, potassium bicarbonate, sodium bicarbonate, and cesium bicarbonate.

7. The method for preparing the intermediate of the uracil compound containing isooxazoline according to claim 6, wherein the alkali is one or two selected from the group consisting of potassium carbonate, sodium carbonate, potassium bicarbonate and sodium bicarbonate, wherein a molar ratio of the alkali to the compound of formula III is 0.5:1-2:1.

8. The method for preparing the intermediate of the uracil compound containing isooxazoline according to claim 1, wherein the reaction is carried out in the presence of a water carrying agent or a mixed solvent that is 2-20 times a weight of the compound of formula III, and the mixed solvent comprises the water carrying agent and a polar aprotic solvent, wherein a weight of the polar aprotic solvent is 20%- 70% of the weight of the mixed solvent.

9. The method for preparing the intermediate of the uracil compound containing isooxazoline according to claim 8, wherein the reaction is carried out in the presence of a water carrying agent selected from the group consisting of n-propyl acetate, isopropyl acetate, n-butyl acetate, methyl isopropyl ketone, methyl isobutyl ketone, ethylene glycol dimethyl ether, ethylene glycol diethyl ether, 2-methyl tetrahydrofuran, and acetonitrile; and the mixed solvent comprises a compound selected from the group consisting of toluene, chlorobenzene, n-propyl acetate, isopropyl acetate, methyl isopropyl ketone, methyl isobutyl ketone, ethylene glycol dimethyl ether, ethylene glycol diethyl ether, 2-methyltetrahydrofuran, and acetonitrile; and the polar aprotic solvent in the mixed solvent is N,N-dimethylformamide, dimethyl sulfoxide, or N-methylpyrrolidone.

10. A method for production of a compound of formula I, comprising: producing a compound of formula II using a method according to claim 1, and converting the compound of formula II to obtain the compound of formula I,

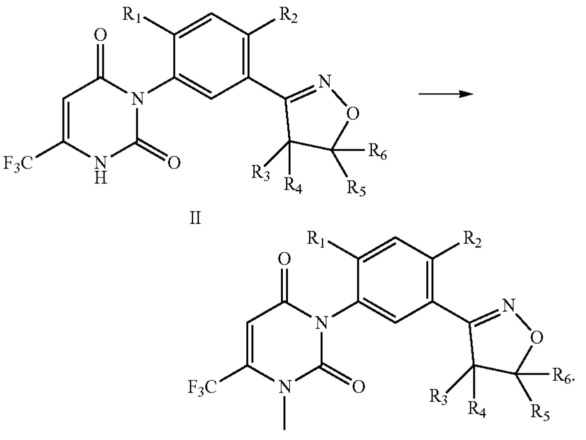

II

I

11. The method for preparing the intermediate of the uracil compound containing isooxazoline according to claim 8, wherein the mixed solvent comprises a compound selected from the group consisting of toluene, chlorobenzene, n-propyl acetate, isopropyl acetate, methyl isopropyl ketone, methyl isobutyl ketone, ethylene glycol dimethyl ether, ethylene glycol diethyl ether, 2-methyltetrahydrofuran, and acetonitrile; and the polar aprotic solvent in the mixed solvent is N,N-dimethylformamide, dimethyl sulfoxide, or N-methylpyrrolidone.

* * * * *